United States Patent

Gall

[11] 3,956,297
[45] May 11, 1976

[54] 9H-DIBENZO[B,F]IMIDAZO[1,2-D][1,4]DIAZEPINES

[75] Inventor: Martin Gall, Kalamazoo, Mich.

[73] Assignee: The Upjohn Company, Kalamazoo, Mich.

[22] Filed: Oct. 2, 1974

[21] Appl. No.: 511,437

Related U.S. Application Data

[63] Continuation-in-part of Ser. No. 424,665, Dec. 14, 1973, abandoned.

[52] U.S. Cl. ............... 260/247.5 EP; 260/239 DD; 260/268 PC; 260/293.6; 260/309; 424/248; 424/250; 424/267; 424/273
[51] Int. Cl.² ........................................ C07D 487/14
[58] Field of Search..... 260/247.5 EP, 309, 268 PC, 260/293.6

[56] References Cited
UNITED STATES PATENTS

| | | | |
|---|---|---|---|
| 3,435,042 | 3/1969 | Drukker et al. | 260/247.5 EP |
| 3,887,575 | 6/1975 | Hester et al. | 260/247.5 EP |

Primary Examiner—Lorraine A. Weinberger
Assistant Examiner—Michael Shippen
Attorney, Agent, or Firm—Hans L. Berneis

[57] ABSTRACT

9H-Dibenzoimidazodiazepine compounds of the formula:

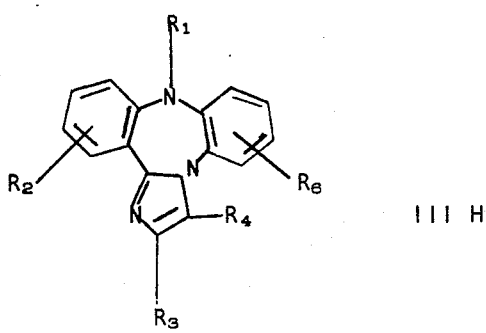

wherein $R_1$ is hydrogen, alkyl,

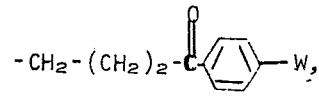

in which W is H, chlorine, or fluorine, or $R_1$ is

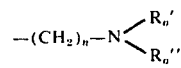

in which n is an integer of 2 to 4, and $R_a'$ and $R_a''$ are hydrogen or alkyl defined as above, or together

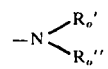

is pyrrolidino, piperidino, N-methylpiperazino, or morpholino, wherein $R_3$ and $R_4$ are hydrogen or alkyl as defined above, or, $R_3$ or $R_4$ can be

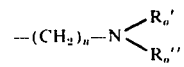

in which

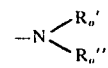

is defined as above and wherein $R_2$ and $R_6$ are selected from the group consisting of hydrogen, halogen, or -$CF_3$, are produced by multistep reactions.

The compounds of the formula above and the pharmacologically acceptable acid addition salts thereof are useful sedatives and anti-depressants. They can also be administered to mammals to alleviate anxieties and produce tranquilization and sedation.

5 Claims, No Drawings

9H-DIBENZO[b, f]IMIDAZO[1,2-d][1,4]DIAZEPINES

CROSS REFERENCE TO RELATED APPLICATION

This application is a continuation in part of application Ser. No. 424,665, filed Dec. 14, 1973, now abandoned.

BACKGROUND OF THE INVENTION

FIELD OF THE INVENTION

This invention is directed to new organic compounds, and more particularly to 9H-dibenzoimidazo compounds, intermediates therefor and a process of production thereof.

The novel compounds, intermediates and processes of production thereof can be illustratively represented by the following schemes of formulae:

Scheme A

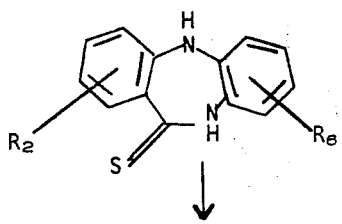

I

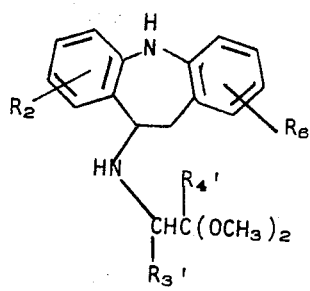

II

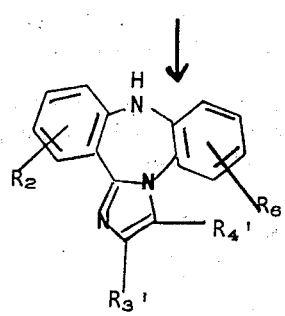

III wherein $R_3'$ and $R_4'$ are hydrogen or alkyl of 1 to 3 carbon atoms, inclusive, and wherein $R_2$ and $R_6$ are hydrogen, halogen, or -$CF_3$.

Compound III can be further modified as shown by Scheme B:

Scheme B

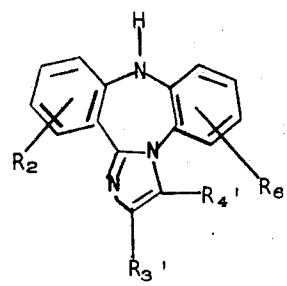

III

RX''

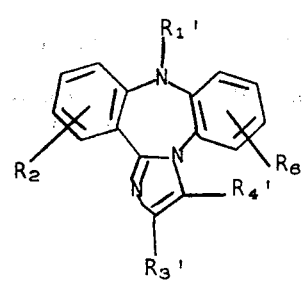

IIIA wherein X'' is bromine or chlorine, wherein $R'_1$ is alkyl of 1 to 3 carbon atoms, inclusive,

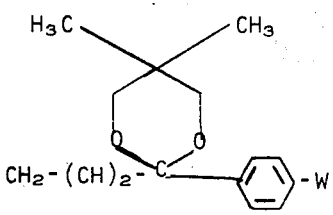

in which W is H, chlorine, or fluorine, or $R_1$ is

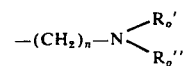

in which n is an integer of 2 to 4 and $R_0'$ and $R_0''$ are hydrogen and alkyl, defined as above, or together

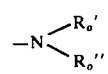

pyrrolidino, piperidino, morpholino, or N-methylpiperazino, and $R_2$ and $R_6$ are defined as in Scheme A, above.

Hydrolysis of those compounds of formula IIIA in which $R_1$ is:

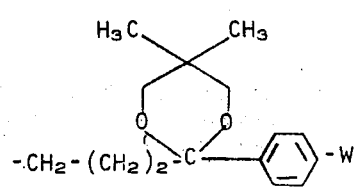

in which W is defined as above, provides compounds of formula IIIB:

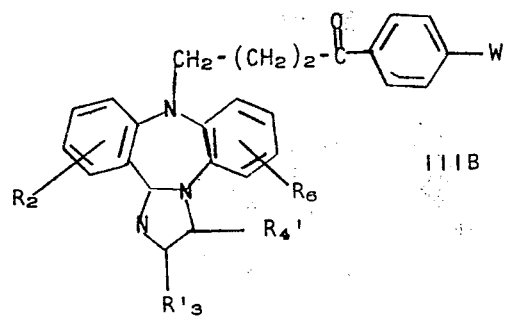

IIIB in which $R_2$, $R_3'$, $R_4'$, $R_6$, and W are defined as herein above.

Compounds of formula III wherein $R_1$ is methyl can also be obtained by the methods of Scheme C.

Scheme C

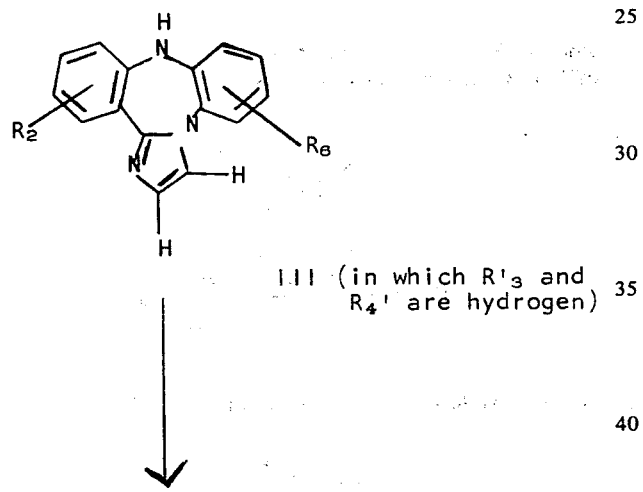

III (in which $R'_3$ and $R_4'$ are hydrogen)

IIIC wherein $R_2$ and $R_6$ are defined as herein above. If an alkyl group is in compound III, compounds such as III D and III E can be produced:

Scheme D

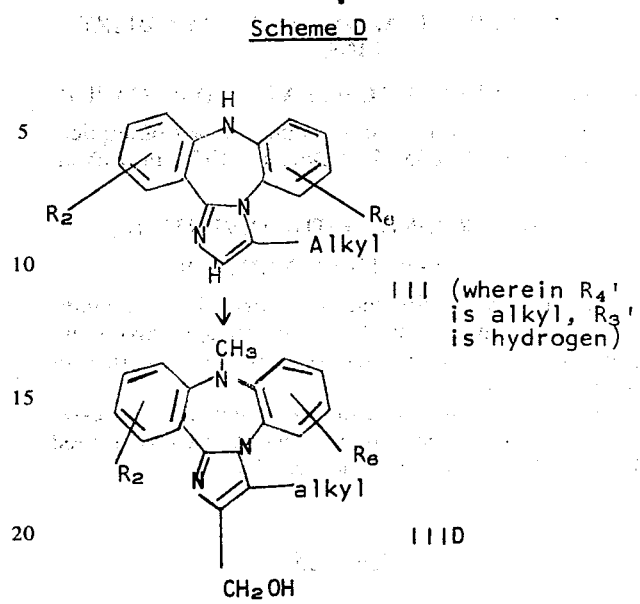

III (wherein $R_4'$ is alkyl, $R_3'$ is hydrogen)

IIID

Scheme E

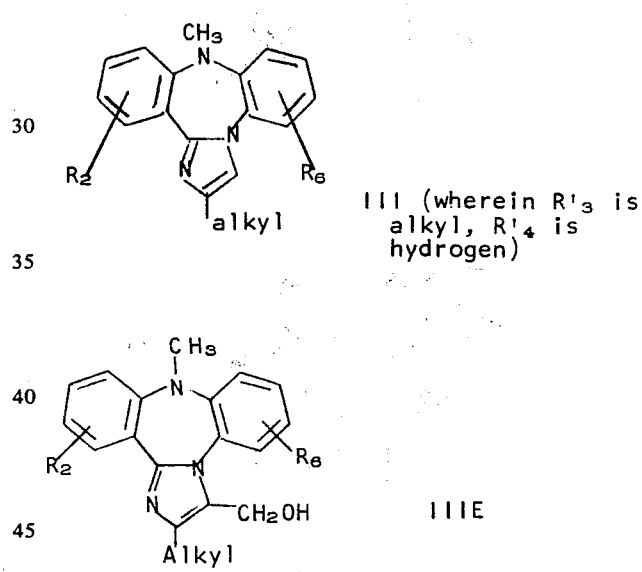

III (wherein $R'_3$ is alkyl, $R'_4$ is hydrogen)

IIIE

For Schemes D and E, $R_2$ and $R_6$ are defined as herein above, and Alkyl of 1 to 3 carbon atoms, inclusive.

A compound of formula III wherein $R_3'$ is alkyl and $R_4'$ is hydrogen can be converted with formaldehyde and a secondary amino compound

in which

is as described herein above, in monoglyme and in the presence of hydrochloric acid, into a compound of formula IIIF:

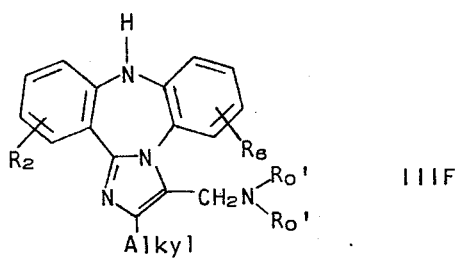

wherein $R_2$ and $R_6$ and alkyl are defined as herein before and wherein

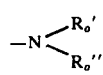

is pyrrolidino, piperidino, morpholino, N-methylpiperazino or dimethylamino.

In the same manner, compound IIIG:

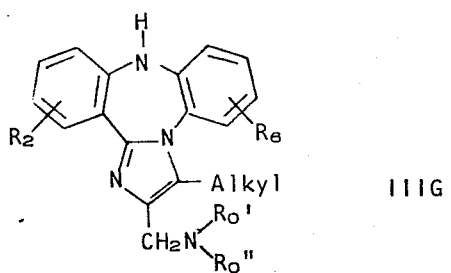

wherein $R_2$, $R_6$, Alkyl and

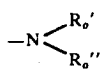

are defined as above, is prepared from compound III, wherein $R_4'$ is alkyl and $R'_3$ is hydrogen.

The compounds of this invention can therefore be represented by the formula IIIH:

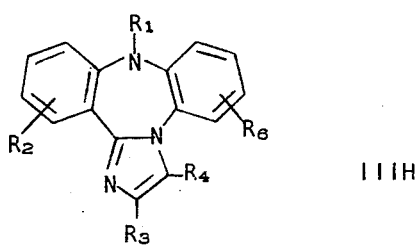

wherein $R_1$ is selected from the group consisting of hydrogen, alkyl of 1 to 3 carbon atoms, inclusive,

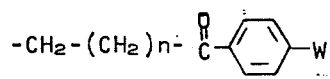

or $R_1$ is

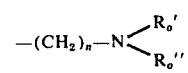

in which n is an integer of 2 to 4, and $R_0'$ and $R_0''$ are hydrogen or alkyl defined as above or, together

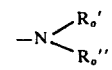

is pyrrolidino, piperidino, N-methylpiperazino, and morpholino; wherein $R_3$ and $R_4$ are hydrogen or alkyl as defined above, or, $R_3$ and $R_4$ can be

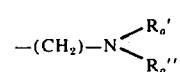

in which

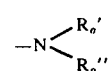

is defined as above; and wherein $R_2$ and $R_6$ are selected from the group consisting of hydrogen, halogen, or $CF_3$, and the pharmacologically acceptable acid addition salts thereof.

The more preferred compounds are those of formula III(I)

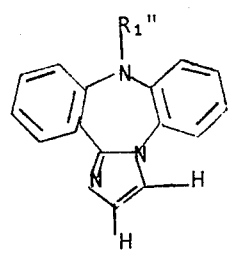

wherein $R''_1$ is alkyl or

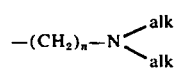

in which n is 2 to 4 and alkyl is in each of 1 to 3 carbon atoms, inclusive, and the pharmacologically acceptable acid addition salts thereof.

Other preferred compounds include those of the formula IIIJ.

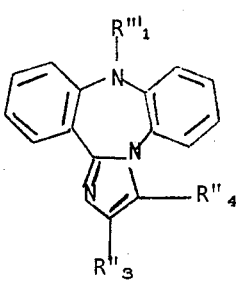

wherein $R_1'''$ is hydrogen or alkyl of 1 to 3 carbon atoms, inclusive, and wherein $R''_3$ and $R''_4$ are hydrogen or alkyl as defined above, or $R''_3$ or $R''_4$ can be

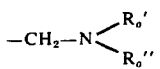

in which $R_0'$ and $R_0''$ are hydrogen or alkyl as defined above, or together

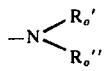

is pyrrolidino, piperidino, N-methylpiperazino, or morpholino, and the pharmacologically acceptable acid addition salts thereof.

The method of scheme A comprises treating a compound of formula 1 with a compound of formula

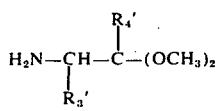

wherein $R_3'$ and $R_4'$ are hydrogen or alkyl of 1 to 3 carbon atoms, inclusive, to give compound II; and treating II with sulfuric acid to obtain a compound of the formula III.

The method of Scheme B comprises: Treating a compound of structure III with a strong base, e.g. sodium hydride, and then with a chloride or bromide of the formula RX'' wherein R is alkyl of 1 to 3 carbon atoms, inclusive,

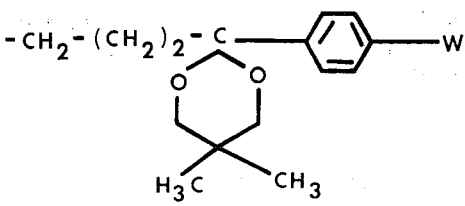

in which W is hydrogen, chlorine, or fluorine, or R is

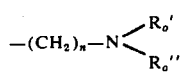

in which n is an integer of 2 to 4, and $R_0'$ and $R_0''$ are hydrogen, or alkyl defined as above, or together

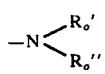

is pyrrolidino, piperidino, morpholino, or N-methylpiperazino, and wherein X'' is chlorine or bromine, to give the compound IIIA.

Hydrolysis of those compounds of formula IIIA in which $R_1$ is defined as above gives the corresponding keto compound.

In the method of schemes C, D, and E a compound of formula III is treated with formaldehyde in formic acid to give a product IIIC or if already methylated in the 2- or 3-position to give a 2- or 3-hydroxymethyl derivative of the compound III, which may additionally be methylated in the 9-position (such as compouns IIIE).

The 2- or 3-hydroxymethyl compounds, IIID or IIIE, can be further treated with triethylamine and methanesulfonyl chloride followed by a secondary amine such as morpholine, pyrrolidine, piperidine, or N-methylpiperazine, to convert the alcoholic group to the corresponding amino group such as seen in compounds IIIF and IIIG.

Compounds IIIF and IIIG can also be directly obtained from a compound of formula III in which $R_3'$ or $R_4'$ is alkyl, by direct reaction of a compound of formula III with formaline, hydrochloric acid and a selected base such as pyrrolidine, piperidine, morpholine, N-methylpiperazine, or dimethylamine, in monoglyme at elevated temperatures.

DESCRIPTION OF THE PREFERRED EMBODIMENT

Lower alkyl groups of 1 to 3 carbon atoms, inclusive, are exemplified by methyl, ethyl, propyl, and isopropyl.

The group $(CH_2)n$ wherein n is 2 to 4 comprises $-(CH_2)_2-$, $-(CH_2)_3-$, or $-(CH_2)_4-$.

Halogen is defined as fluorine, chlorine, or bromine.

The novel compounds IIIH of this invention are agents for tranquilization and as antidepressants. They can be used in mammals and birds, particularly for animals in transport, like for zoo animals, e.g. lions, tigers, elephants, parrots; farm animals, e.g. cattle, sheep, swing, or domestic pet animals e.g. cats and dogs.

The new compounds were tested for sedative and antidepressant activity in laboratory animals as follows:

SEDATION-TRANQUILIZATION

Chimney test — [Med. Exp. 4, 145 (1961)]: The test determines the ability of mice to back up and out of a vertical glass cylinder within 30 seconds. At the effective dosage, $ED_{50}$, 50% of the mice failed doing it.

Dish test — Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test — The untreated mouse leaves a standard pedestal in less than a minute to climb back to the floor of the standard mouse box. Tranquilized mice will stay on the pedestal for more than 1 minute.

Nicotine antagonism test — Mice in a group of 6 are injected with the test compound. Thirty minutes later the mice including control (untreated) mice are injected with nicotine salicylate (2 mg./kg.). The control mice show over-stimulation, i.e., (1) running convulsions followed by (2) tonic extensor fits; followed by (3) death.

THE ANTIDEPRESSANT ACTION

The main function of an antidepressant is to return the depressed individual up to normal function. This should be carefully differentiated from psychic stimulants such as the amphetamines which produce over-stimulation in the normal individual.

Many different methods have been and are used to evaluate antidepressant activity. In general these methods involve antagonism to a depressant such as reserpine or tetrabenazine or a synergistic increase of the toxicity of certain compounds (i.e., yohimbine or 3,4-dihydroxyphenylalanine) and comparison of the drug action of the new compound with other known antidepressants. No single test alone can determine whether or not a new compound is an antidepressant or not, but the profile evidenced by various tests will establish the anti-depressant action if present. A number of such tests are described below.

Hypothermic tests with oxotremorine: [1-[4-(pyrrolidinyl)-2-butynyl]-2-pyrrolidinone].

Oxotremorine (as well as apomorphine and tetrabenazine) produces hypothermic responses in mice. This response is blocked by anticholinergics and antidepressants such as atropine and imipramine.

Oxotremorine produces a very pronounced hypothermia which reaches a peak 60 minutes after administration.

At 0.6 mg./kg. the body temperature of a mouse is decreased about 13° F. (when the mouse is kept at room temperature). This temperature decrease is antagonized by anti-depressants e.g. desipramine, imipramine, doxepine, and others.

The present compounds were tested as follows. Four male mice of 18–22 g. (Strain CF=Carworth Farms) were injected intraperitoneally with 1 mg. of oxotremorine. The lowering of the body temperature was measured rectally with an electronic thermometer, before and 30 minutes after drug administration. After the drug administration the mice were kept at 19° C. in cages. A raise of 4° Fahrenheit over the oxotremorine-produced lowered body temperature was taken as indicative of anti-depressant activity.

Potentiation of yohimbine aggregation toxicity: the $LD_{50}$ of yohimbine hydrochloride in mice is 45 mg./kg. i.p. Administration of 30 mg./kg. of yohimbine hydrochloride was non-lethal. If an antidepressant is administered prior to the yohimbine hydrochloride (30 mg.), the lethality of the yohimbine hydrochloride is increased.

Ten male CF mice, 18–22 g., were injected with yohimbine hydrochloride in saline solution. After two hours the $LD_{50}$ are determined. Groups of ten mice are injected with the antidepressant 30 minutes before the administration of yohimbine hydrochloride [YCl] (30 mg.). No mice or only one mouse is killed from 30 mg. of [YCl]. If [YCl] is administered in the presence of an anti-depressant an increase in the toxicity of [YCl] is found. $ED_{50}$ value of the test compound is the dosage which causes 50% of the mice to die.

Potentiation of apomorphine gnawing: a group of 4 mice (male, CF, 18–22 g.) are administered the test compound intraperitoneally 1 hour prior to the subcutaneous injection of apomorphine hydrochloride 1 mg./kg. The mice are then placed in a plastic box (6 inches × 11 inches × 5 inches) lined at the bottom with a cellophane-based, absorbent paper. The degree of damage to the paper at the end of 30 min. is scored from zero to 4. The scores 3 and 4 indicate that the compound is a potentiator of apomorphine in this test. Positive tests in this series show that the new compounds have anxiolytic antidepressant and tranquilizing sedative action.

The pharmaceutical forms of compounds of formula IIIH (including IIIB, IIIC, IIID, IIIE, IIIF, and IIIG, and the preferred compounds III(I) and IIIJ, and salts thereof) contemplated by this invention, include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates, lactose, proteins, lipids, calcium phosphate, cornstarch, stearic acid, methylcellulose and the like may be used as carriers or for coating purposes. Water or oils such as coconut oil, sesame oil, safflower oil, cottonseed oil, and peanut oil, may be used for preparing solutions or suspensions of the active drug. Sweetening, coloring, and flavoring agents may be added.

For mammals food premixes with starch, oatmeal, dried fishmeat, fishmeal, flour, and the like can be prepared.

As sedatives and antidepressants the compounds of formulae III (including IIIA through IIIH) and their pharmacologically acceptable acid addition salts can be used in dosages of 0.2–30 mg./kg.; preferably from 1.0 to 10 mg./kg. in oral in injectable preparations as described above to alleviate anxieties and depression occurring in stressful situations. Such situations are those for example, when animals are changing ownerships or are temporarily put into kennels while their owners are absent from home, or are traveling.

Acid addition salts of the compounds of formula III (and IIIB, C, D, E, F, G, H, I and J) can be made, such as the flosilicic acid addition salts which can be applied as mothproofing agents, and salts with trichloracetic acid, useful as herbicides against Johnson grass, Bermuda grass, yellow and red foxtail, and quack grass.

The starting materials of this invention are dihydrodibenzodiazepinethiones I which are either known or can be synthesized, for e.g. by treating the corresponding oxo compounds [Arzneim. Forschung 13, 324 (1963)] with phosphorus pentasulfide as further illustrated by the Preparations.

In carrying out the process of this invention according to scheme A, a selected thione I is heated for 1 to 12 hours with an aminoacetaldehyde dimethylacetal of the formula:

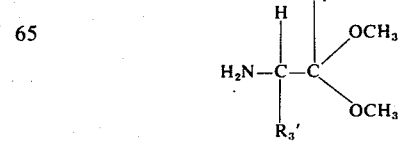

wherein $R_3'$ or $R_4'$ is hydrogen or alkyl of 1 to 3 carbon atoms, inclusive. The reaction is conveniently carried out in an inert organic solvent such as ethanol, 1-propanol, 2-propanol, 1- and 2-butanol, tetrahyrdofuran, dioxane or the like, the resulting product II is obtained by conventional procedures, such as removal of solvents by evaporation, preferably in vacuo, extraction, chromatograpahy, and crystallization.

Compound II is then cyclized preferably in concentrated sulfuric acid between 0° to 35° C. during 1/2 to 6 hours. The product III is produced by quenching the sulfuric acid reaction mixture cautiously in cold water and neutralizing the resulting precipitated slurry with sodium or potassium hydroxide or carbonate. From this mixture the product III is extracted with an organic solvent e.g. chloroform, methylene chloride, benzene or the like, and the pure product III is obtained by conventional procedures, such as removal of the solvents by evaporation, preferably in vacuo, extraction, chromatography, and crystallization.

Carrying out the method B, a chloro or bromo organic compound such as an alkyl chloride, a dialkyl-aminoalkyl chloride, or a pyrrolidino, piperidino, morpholino, or piperazino alkyl chloride or bromide or a halide compound of the formula

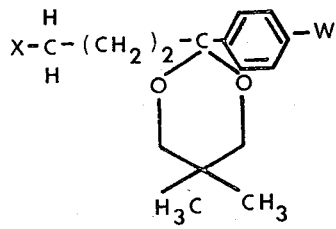

wherein W is hydrogen, chlorine, or fluorine and X' is chlorine, or bromine, is treated with a compound of formula III in the presence of a strong base such as sodium or potassium hydride. Equimolar amounts of the strong base, compound III and the organic chloride or bromide are used in this reaction.

The reaction, first between Compound III and the base, is carried out at a temperatuare of 60°–120° C during a period of 10–60 minutes and is continued with the addition of the reactant organic chloride or bromide at the same temperature for 1–6 hours. After the reaction is terminated the product IIIA is obtained by conventional procedure such as extractions, chromatography, crystallization, and the like.

In methods C, D, E, a 2- or 3-alkyl compound III is reacted with formaldehyde in formalin (37% aqueous formaldehyde). The reaction is best carried out at the boiling temperature of the mixture i.e. near 100° C. for a period of 1–48 hours the products IIIC, IIID, or IIIE are recovered from the reaction mixture by conventional procedures such as extraction, chromatography, and crystallization.

Alternatively a compound of formula IIIF is prepared by treating a compound of formula III wherein $R_3'$ is alkyl and $R_4'$ is hydrogen, with formalin, a compound selected from pyrrolidine, piperidine, morpholine, dimethylamine or diethylamine, in the presence of hydrochloric acid, in monoglyme. In the preferred method of the invention, the mixture is heated for 12–48 hours on a steam bath at 100° C. However, temperatures between 60°–130° C. are suitable. The product is separated and purified by standard procedures such as extraction, concentration, recrystallization, and chromatography.

Preparation 1 — 7-Chloro-5,10-dihydro-11H-dibenzo[b,e]-[1,4]diazepine-11-thione

A mixture of 7-chloro-5,10-dihydro-11H-dibenzo[b,e]-[1,4]diazepin-11-one (30.5 g., 0.125 mole), phosphorus pentasulfide (27.8 g., 0.131 mole) and one l. of pyridine is heated at reflux temperature for 4 hours and the pyridine is evaporated in vacuo. The residue is stirred for 1 hour with one l. each of saturated aqueous sodium bicarbonate and methylene chloride and filtered to remove some solid product. The organic layer of the filtrate is washed successively with sodium bicarbonate solution and with saturated salt solution, dried over anhydrous magnesium sulfate and evaporated. The residue is combined with the solid obtained above and triturated with hot chloroform and methanol. In this way, 12.2 g. of 7-chloro-5,10-dihydro-11H-dibenzo[b,e][1,4]diazepine-11-thione of melting point 274°–275° C is obtained. Concentration of the chloroform-methanol washings affords an additional 8.4 g. of product having the same melting point. Recrystallization from dimethylformamide-water gives an analytically pure sample in the form of pale yellow needles of melting point 276°–277° C.

Preparation 2 — 5,10-Dihydro-5-methyl-11H-dibenzo[b,e]-[1,4]diazepine-11-thione

A mixture of 5,10-dihydro-5-methyl-11H-dibenzo[b,e]-[1,4]diazepin-11-one (6.1 g., 0.0272 mole), phosphorus pentasulfide (6.51 g., 0.0286 mole) and 175 ml. of pyridine is heated at reflux temperature for 3.75 hours and the pyridine is then evaporated in vacuo. The residue is shaken with chloroform and saturated aqueous sodium bicarbonate. The resulting suspension is filtered to give solid A. The chloroform layer of the filtrate is washed successively with saturated aqueous sodium bicarbonate and with saturated salt solution, dried over anhydrous magnesium sulfate and evaporated. The residue is crystallized from methylene chloride-methanol to give 3.5 g. of 5, 10-dihydro-5-methyl-11H-dibenzo[b,e][1,4]diazepin-11-thione of melting point 217°–218° C., which is unchanged after recrystallization. A second crop weighs 0.8 g. and melts at 214°–215° C.

Solid A is shaken with methylene chloride and 10% sodium hydroxide and processed as above to give an additional 1.5 g. of the thione, at melting point 216°–217° C.

Anal. calcd. for $C_{14}H_{12}N_2S$: C, 69.96; H, 5.30; N, 11.66; S, 13.34; Found: C, 69.79; H, 5.20; N, 11.37; S, 13.29.

In the same manner shown by the above preparation, other starting compounds can be obtained, such as:
2-chloro-5,10-dihydro-11H-dibenzo[b,e][1,4]diazepine-11-thione;
3-chloro-5,10-dihydro-11H-dibenzo[b,e][1,4]diazepine-11-thione;
7-dichloro-5,10-dihydro-11H-dibenzo[b,e][1,4]diazepine-11-thione;
6-chloro-5,10-dihydro-11H-dibenzo[b,e][1,4]diazepine-11-thione;
2,8-bromo-5,10-dihydro-11H-dibenzo[b,e][1,4]diazepine-11-thione;
8-ethyl-5,10-dihydro-11H-dibenzo[b,e][1,4]diazepine-11-thione;

8-chloro-5,10-dihydro-11H-dibenzo[b,e][1,4]diazepine-11-thione;
5,10-dihydro-8-trifluoromethyl-11H-dibenzo[b,e][1,4]diazepine-11-thione;
5,10-dihydro-7-methoxy-11H-dibenzo[b,e][1,4]diazepine-11-thione;
5,10-dihydro-3-methoxy-11H-dibenzo[b,e][1,4]diazepine-11-thione;
3-methyl-5,10-dihydro-11H-dibenzo[b,e][1,4]diazepine-11-thione;
5,10-dihydro-8-propyl-11H-dibenzo[b,e][1,4]diazepine-11-thione;
8-fluoro-5,10-dihydro-11H-dibenzo[b,e][1,4]diazepine-11-one;
and the like.

EXAMPLE 1

[(5H-dibenzo[b,e][1,4]diazepine-11-yl)amino]-acetaldehyde dimethyl acetal 5,10-Dihydro-11H-dibenzo[b,e][1,4]diazepine-11-thione (33.75 g., 150 mmol.) is suspended in 450 ml. of n-butyl alcohol and treated with 47.25 g. (450 mmol.) of commerical aminoacetaldehyde dimethyl acetal. The reagents are heated for 5.5 hours during which time the solution turns brown. The solution is cooled to room temperature and the solvent is removed in vacuo. The residue is dissolved in 600 ml. of hot ethyl acetate, filtered, concentrated to 400 ml. and cooled to give 36.0 g. (81%) of [(5H-dibenzo[b,e][1,4]diazepin-11-yl)amio]acetaldehyde dimethyl acetal of melting point 181°–182.5° C. A second crop (2.55 g., 5.7%) of melting point 181.5°–184° C. is also collected.

Anal. calcd. for $C_{17}H_{19}N_3O_2$: C, 68.66; H, 6.44; N, 14.13 Found: C, 68.52; H, 6.55; N, 14.10.

EXAMPLE 2

9H-Dibenzo[b,f]imidazo[1,2-d][1,4]diazepine

[(5H-dibenzo[b,e][1,4]diazepine-11-yl)amino]acetaldehyde dimethyl acetal (30.0 g., 101.0 mmol.) is dissolved in 100 ml. of concentrated sulfuric acid and stirred at room temperature for 3 hours. The product is isolated by pouring the acid solution cautiously, and in portions into ice-cold distilled water, and carefully adding the resulting slurry to 3.0 L. of cold 10% aqueous sodium hydroxide solution. The product is extracted with chloroform; the chloroform layer is back-extracted with 10% aqueous sodium hydroxide followed by washing with a brine soltuion and then the chloroform solution is dried over magnesium sulfate. After filtration and concentration in vacuo, a residue is obtained, which is dissolved in 800 ml. of hot ethyl acetate, filtered to remove insoluble material, and then concentrated to a volume of 500 ml. On colling, 16.34 g. (70.0%) of 9H-dibenzo[b,f]imidazo[1,2-d][1,4]diazepine of melting point 215°–217° C. is obtained in the form of prisms. An additional 5.23 g. (22.4%) of product is obtained in two additional crops.

Anal. calc. for $C_{15}H_{11}N_3$: C, 77.23; H, 4.75; N, 18.01. Found: C, 76.93; H, 4.92; N, 17.90.

EXAMPLE 3

2-Methyl-9H-dibenzo[b,f]imidazo[1,2-d][1,4]-diazepine

A. In a 250-ml., three-neck flask fitted with a condenser, is heated to reflux 6.25 g. of 5,10-dihydro-11H-dibenzo-[b,e][1,4]diazepine-11-thione (30.0 mmol.) and 10.8 g. of aminopropionaldehyde dimethyl acetal (90.0 mmol.) in 60 ml. of n-butanol, during 2 hours. An additional 60 ml. of n-butanol is added and the mixture is refluxed overnight (22 hours). At this point, 60 ml. of n-butanol is distilled from the reaction mixture and refluxing is maintained for an additional 18 hours. On cooling, 2.0 g. of crude starting material is obtained. This is added to the reaction mixture along with an additional 5.4 g. of aminopropionaldehyde acetal (40.0 mmol.) and heating is maintained over a weekend (65 hours). On cooling and removal of the solvent in vacuo, 10 g. of brown oil is obtained. The oil is dissolved in 80 ml. of concentrated sulfuric acid and stirred at room temperature under nitrogen for 10 hours. The reaction mixture is then poured into ice and carefully neutralized with 50% aqueous sodium hydroxide solution. The basic aqueous solution is extracted thoroughly with chloroform. The combined chloroform extracts are washed with brine, dried over anhydrous potassium carbonate and concentrated in vacuo. The resulting oil is taken up in ethyl acetate, treated with activated charcoal and filtered. On concentrating and cooling the filtered solution, 3.2 g. of 2-methyl-9H-dibenzo[b,f]imidazo[1,2-d][1,4]diazepine is obtained in 2 crops (yield 40%) of melting point 232°–236° C.

B. A suspension of 67 g. (0.3 mol.) of 5,10-dihydro-11H-dibenzo[b,e][1,4]diazepine-11-thione 72 g., (0.6 mol.) of aminopropionaldehyde dimethyl acetal and 300 ml. of diethylene glycol is heated to 190° in a 1 l-flask and kept under nitrogen for 24 hours, by which time, nearly all the starting material is consumed. The solution is cooled to room temperature and treated with 50 ml. of concentrated sulfuric acid for 2 hours. The reaction mixture is then permitted to stir overnight, and is then worked up by pouring onto ice and neutralizing with a 50% sodium hydroxide solution. The product is extracted with chloroform, washed with water and dried over anhydrous potassium carbonate. On evaporating the solvent in vacuo, a brown oil is obtained which is crystallized to give 15 g. of 2-methyl-9H-dibenzo-[b,f]imidazo[1,2-d][1,4]diazepine (20.2%) in the form of yellow prisms, of melting point 233°–235° C.

Anal. calcd. for $C_{16}H_{13}N_3$: C, 77.71; H, 5.30; N, 16.99. Found: C, 77.49; H, 5.49; N, 17.44.

EXAMPLE 4

7-chloro[(5H-dibenzo[b,e][1,4]diazepin-11-yl)-amino]acetalde dimethyl acetal.

In the manner given in Example 1, 7-chloro-5,10-dihydro-11H-dibenzo[b,e][1,4]diazepine-11-thione is treated with aminoacetaldehyde dimethyl acetal in n-butanol to give 7-chloro-[(5H-dibenzo[b,e][1,4]diazepin-11-yl)amino]-acetaldehyde dimethyl acetal.

EXAMPLE 5

7-Chloro-9H-dibenzo[b,e]imidazo[1,2-d][1,4]-diazepine

In the manner given in Example 2, 7-chloro-[(5H-dibenzo[b,e][1,4]diazepin-11-yl)amino]acetaldehyde dimethyl acetal is treated with concentrated sulfuric acid to give 7-chloro-9H-dibenzo[b,f]imidazo[1,2-d][1,4]diazepine.

EXAMPLE 6

8-Trifluoromethyl-[(5H-dibenzo[b,e][1,4]diazepin-11-yl)amino]acetaldehyde dimethyll acetal In the manner given in Example 1, 8-trifluoromethyl-5,10-dihydro-11H-dibenzo[b,e][1,4]diazepine-11-thione is treated with amino acetaldehyde dimethyl acetal in n-butanol to give 8-trifluoromethyl-[(5H-dibenzo[b,e][1,4]diazepin-11-yl)amino]acetaldehyde dimethyl acetal.

EXAMPLE 7

6-trifluoromethyl-9H-dibenzo[b,f]imidazo[1,2-d]-[1,4]diazepine

In the manner given in Example 5, 8-trifluoromethyl-[(5H-dibenzo[b,e][1,4]diazepin-11-yl)amino]acetaldehyde dimethyl acetal is treated with concentrated sulfuric acid to give 6-trifluoromethyl-9H-dibenzo[b,f]imidazo-[1,2-d][1,4]diazepine.

EXAMPLE 8

2-chloro-[(5H-dibenzo[b,e][1,4]diazepin-11-yl)-amino]acetaldehyde dimethyl acetal In the manner given in Example 4, 2-chloro-5,10-dihydro-11H-dibenzo[b,e][1,4]diazepine-11-thione is treated with amino acetaldehyde dimethyl acetal in n-butanol to give 2-chloro-[(5H-dibenzo[b,e][1,4-]diazepin-11-yl) amino]-acetaldehyde dimethyl acetal.

EXAMPLE 9

12-chloro-9H-dibenzo[b,f]imidazo[1,2-d][1,4]-diazepine

In the manner given in Example 5, 2-chloro-[(5H-dibenzo[b,e][1,4]diazepin-11-yl)amino]acetaldehyde dimethyl acetal is treated with concentrated sulfuric acid to give 12-chloro-9H-dibenzo[b,f]imidazo[1,2-d][1,4]diazepine.

EXAMPLE 10

8-methyl-[(5H-dibenzo[b,e][1,4]diazepin-11-yl)-amino]acetaldehyde dimethyl acetal In the manner given in Example 4, 8-methyl-5,10-dihydro-11H-dibenzo[b,e][1,4]diazepine-11-thione is treated with amino acetaldehyde dimethyl acetal in n-butanol to give 8-methyl-[(5H-dibenzo[b,e][1,4-]diazepin-11-yl)amino]-acetaldehyde dimethyl acetal.

EXAMPLE 11

6-methyl-9H-dibenzo[b,f]imidazo[1,2-d][1,4]-diazepine

In the manner given in Example 5, 8-methyl-[(5H-dibenzo[b,e][1,4]diazepin-11-yl)amino]acetaldehyde dimethyl acetal is treated with concentrated sulfuric acid to give 6-methyl-9H-dibenzo[b,f]imidazo[1,2-d][1,4]diazepine.

EXAMPLE 12

3-methoxy-[(5H-dibenzo[b,e][1,4]diazepin-11-yl)amino]acetaldehyde dimethyl acetal In the manner given in Example 4, 3-methoxy-5,10-dihydro-11H-dibenzo[b,e][1,4]diazepine-11-thione is treated with amino acetaldehyde dimethyl acetal in n-butanol to give [(5H-dibenzo[b,e][1,4]diazepin-11-yl)amino]acetaldehyde dimethyl acetal.

EXAMPLE 13

11-methoxy-9H-dibenzo[b,f]imidazo[1,2-d][1,4]-diazepine

In the manner given in Example 5, 3-methoxy[(5H-dibenzo[b,e][1,4]diazepin-11-yl)amino]acetaldehyde dimethylacetal is treated with concentrated sulfuric acid to give 11-methoxy-9H-dibenzo[b,f]imidazo[1,2-d][1,4]diazepine.

EXAMPLE 14

3-methyl-9H-dibenzo[b,f]imidazo[1,2-d][1,4]diazepine In the manner given in example 3 B, a suspension of 5,10-dihydro-11H-dibenzo[b,e][1,4]diazepine-11-thione and aminoacetone ethylene ketal in diethylene glycol is heated to 190° C. for 24 hours, cooled to room temperature, and treated with concentrated sulfuric acid to give 3-methyl-9H-dibenzo[b,f]imidazo[1,2-d][1,4]diazepine.

EXAMPLE 15

9-Methyl-9H-dibenzo[b,f]imidazo[1,2-d][1,4]-diazepine

9H-Dibenzo[b,f]imidazo[1,2-d][1,4]diazepine (2.35 g., 10 mmol.) is dissolved in 13.0 g. of 88% formic acid (150 mmol.), treated with 6.75 ml. of 37% aqueous formalin solution (90.0 mmol.) and heated for 22 hours at 100° C. At the end of this period, the reaction is permitted to cool to room temperature, poured into 200 ml. of cold 5% aqueous sodium hydroxide, extracted with methylene chloride, dried over anhydrous magnesium sulfate, and concentrated in vacuo to give an oil which crystallized from ethyl acetate to give 1.76 g. (71.0%) of 9-methyl-9H-dibenzo[b,f]imidazo[1,2-d][1,4]diazepine of melting point 194.5°–197° C.

Anal. calcd. for $C_{16}H_{13}N_3$: C, 77.71; H, 5.30; N, 16.99. Found: C, 77.45; H, 5.39; N, 16.92.

EXAMPLE 16

9-[2-(dimethylamino)ethyl]-9H dibenzo[b,f]-imidazo[1,2-d][1,4]diazepine dihydrobromide 9H-dibenzo[b,f]imidazo[1,2-d][1,4]diazepine (1.17 g., 5.0 mmol.) is dissolved in 50 ml. of dimethyl formamide, treated with 250 mg. of a 57% sodium hydride dispersion (in oil, 6.0 mmol. of reagent) and heated to 95° C. for 30 min. A deep red color of the anion formed. To this solution is added rapidly, on one portion, a solution of 2.7 g. of dimethylaminoethyl chloride (12.5 mmol.) in 50% wt/wt xylene. Within 5 minutes, a precipitate forms and the red color of the anion is replaced by a brown solution. Heating is maintained for 4–5 hours, at which time the heater is removed and the reaction is permitted to stand overnight. The solid is filtered and dried over anhydrous sodium sulfate and the solution is concentrated to dryness in vacuo. The resulting oil is taken up in 25 ml. of methylene chloride and 25 ml. of water. The layers are separated and the aqueous layer is extracted with four 20 ml. portions of methylene chloride. The combined organic layers are washed with a saturated aqueous sodium chloride solution, dried over anhydrous magnesium sulfate, and concentrated in vacuo. The hydrobromide salt is formed in ethyl acetate/ethanol and 700 mg. of 9-[2-(dimethylamino)ethyl]-9H-dibenzo[b,f]imidazo]1,2-d][1,4]diazepine dihydrobromide of melting point 270°–272° is collected. A portion is recrystallized from 2-propanol to give 200 mg. of melting point 269°–270° C. containing 0.61% 2-propanol (melt solvate).

Anal. calcd. for $C_{19}H_{22}Br_2N_4$: C, 48.94; H, 4.75; N, 12.02; Br 34.28 Found: C, 48.70; H, 4.88; N, 12.03; Br, 33.75.

EXAMPLE 17

9-[3-(Dimethylamino)propyl]-9H-dibenzo-[b,f]imidazo[1,2-3][1,4]diazepine dihydrobromide 9H-dibenzo[b,f]imidazo[1,2-d][1,4]diazepine (1.17 g., 5.0 mmol.) is dissolved in 50 ml. of dimethyl formamide, treated with 250 mg. of a 57% sodium hydride dispersion (in oil) (6.0 mmol. of reagent), and heated to 95° C. for 30 minutes. To the red solution of the anion is added rapidly and in one portion a solution of 3.06 g. (12.5 mmol.) of dimethylaminopropyl chloride in 3.06 g. of xylene. A precipitate forms and the red color of the anion is replaced by a dark blue solution, the color of which gradually disappears on heating. After 6 hours the mixture is cooled to room temperature and the solid is filtered off and washed with chloroform. The dimethyl formamide is removed in vacuo and the residue is treated with 25 ml. of methylene chloride and 25 ml. of water. The aqueous layer is further extracted with methylene chloride and the combined organic extract is washed in a saturated aqueous sodium chloride solution, dried and concentrated in vacuo. The oil is converted to its dihydrobromide salt and crystallized from ethyl acetate/ethanol to give 500 mg. of yellow solid. This solid is recrystallized from isopropanol (200 mg. of solid in 10 ml. of solvent) to give 90 mg. of 9-[2-(dimethylamino)propyl]-9H-dibenzo[b,f]imidazo[1,2-d][1,4]diazepine dihydrobromide in crystalline form of melting point 268°–269° C. (decomposed). In the same way, 220 mg. of pure product is obtained from the remaining 300 mg. of crude product.

Anal. calcd. for $C_{20}H_{24}N_4Br_2$: C, 50,02; H, 5.04; N, 11.66; Br, 33.28. Found: C, 50.06; H, 5.08; N, 11.71; Br, 30.87.

EXAMPLE 18

9-[3-[2-(p-fluorophenyl)]-5,5-dimethyl-m-dioxan-2-yl]propyl]-9H-dibenz[b,f]imidazo[1,2-d][1,4]diazepine   9H-dibenzo[b,f]imidazo[1,2-d][1,4]diazepine (7.0 g., 30.0 mmol.) is dissolved in 250 ml. of dimethylformamide, treated with 1.5 g. of a 57% sodium hydride in oil dispersion (0.855 g., 37.6 mmol. of reagent) and heated to 95° C. for 0.5 hours. To the red solution of the anion is added 7.5 g. of ω-chloro-p-fluorobutyrophenone dimethyl ketal (30.0 mmol.) dissolved in 50 ml. of dimethylformamide and the solution is heated for 2 hours. Analysis of a aliquot indicated that some starting material is still present; therefore an additional 1.5 g. (6.5 mmol.) of ω-chloro-p-fluorobutyrophenone dimethyl ketal is added along with potassium iodide (2.4 g., 14.5 mmol.) and the mixture is heated at 95° C., for an additional two hours. During this heating period, the red color of the anion disappears. The reaction mixture is permitted to stir overnight at room temperature and is the poured into ice, made basic with an aqueous 5% sodium hydroxide solution and extracted with chloroform. The chloroform extract is washed with water, dried over anhydrous sodium sulfate and concentrated in vacuo to yield a pink oil. The product is chromatographed on 1 kg. of silica gel using a 50% ethyl acetate/cyclohexane solution as eluent. The product is collected in fractions 11 to 30 (200 ml. fractions are collected) and crystallized by trituration with a mixture of petroleum ether and ether to give 12 g. (86%) of 9-[3-[2-(p-fluorophenyl]-5,5-dimethyl-m-dioxan-2-yl]propyl]-9H-dibenz[b,f]imidazo-[1,2-d][1,4]diazepine as a white powder of melting point 138°–140° C.

Anal. calcd. for $C_{30}H_{30}FN_3O_2$: C, 74.51; H, 6.25; N, 8.69; F, 3.93 Found: C, 74.30; H, 6.22; N, 8.51; F, 3.99.

EXAMPLE 19

4'-Fluoro-4-[(9H-dibenzo[b,f]imidazo[1,2-d]-[1,4-diazepin-9-yl]butyrophenone

A solution of 2.0 g. (4.0 mmol.) of 9-[3-[2-(p-fluorophenyl)-5,5-dimethyl-m-dioxan-2-yl]propyl]-9H-dibenz-[b,f]imidazo[1,2-d][1,4]diazepin in 20 ml. of methanol is treated with 5.0 ml. of 2N hydrochloric acid and stirred at room temperature overnight. It is poured into an ice-water mixture, neutralized with a 5% aqueous sodium hydroxide solution and extracted with ether. The ether solution is dried over anhydrous sodium sulfate and concentrated in vacuo to yield a white solid which crystallized from ethyl acetate to afford 900 mg. of 4'-fluoro-4(9H-dibenzo-[b,f]imidazo[1,2-d][1,4]diazepin-9-yl)butyrophenone of melting point 163°–165°.

Anal. calcd. for $C_{25}H_{20}FN_3O$: C, 75.55; H, 5.07; N, 10.58; F, 4.78. Found: C, 75.51; H, 5.00; N, 10.55; F, 4.70.

EXAMPLE 20

2,9-Dimethyl-3-hydroxymethyl-9H-dibenzo[b,f]-imidazo[1,2-d][1,4]diazepine

2-Methyl-9H-dibenzo[b,f]imidazo[1,2-d][1,4]diazepine (0.4925 g., 2.00 mmol.) is dissolved in 2.62 g. of 88% formic acid, treated with 1.35 ml. of a 37 % aqueous formalin solution and heated for 22.5 hours, then quenched in a cold 5% aqueous sodium hydroxide solution, extracted with chloroform, dried over anhydrous magnesium sulfate and concentrated in vacuo. Crystallization of the product from ethyl acetate/hexane afforded 270 mg. (41.3%) of 2,9-dimethyl-3-hydroxymethyl-9H-dibenzo [b,f]imidazo[1,2-d][1,4]diazepine of melting point 187°–190° C. in the form of white needles.

Anal. calcd. for $C_{18}H_{17}N_3O$: C, 74.20; H, 5.88; N, 14,43. Found: C, 74.06; H, 6.01; N, 14.14.

EXAMPLE 21

2-Methyl-3-(1-pyrrolidinylmethyl)-9H-dibenzo-[b,f]imidazo[1,2-d][1,4]diazepine

A mixture of 1.2 ml. of a 37% aqueous formalin (14.8 mmol.) solution. 0.50 ml. (0.426 g., 6.0 mmol.) of pyrrolidine, 3.0 ml. of 2N hydrochloric acid, dissolved in 4.0 ml. of monoglyme is placed in a 20 ml. round bottom flask. To the magnetically stirred solution is added 0.4925 g. of 2-methyl-9H-dibenzo[b,-f]imidazo[1,2-d][1,4]diazepine (2.00 mmol.) and the solution is heated on a steam bath overnight (22 hrs.). The entire reaction mixture is worked up by quenching in a cold 5% aqueous sodium hydroxide solution, extracting with chloroform, drying over anhydrous sodium sulfate and concentrating in vacuo to a yellow oil. The oil is taken up in ethyl acetate and filtered from a small amount of floculent white solid. The product crystallized from ethyl acetate/hexane to give 200 mg. (30.2%) of 2-methyl-3-(1-pyrrolidinylmethyl)-9H-dibenzo-[b,f]imidazo[1,2-d][1,4]diazepine of melting point 217°–220° C. (decomposed). A portion is recrystallized from ethyl acetate/hexane to give the desired product in the form of prisms of melting point 225°–228° C. decomp.

Anal. Calcd. for $C_{21}H_{22}N_4$: C, 76.33; H, 6.71; N, 16.96. Found: C, 76.29; H, 6.97; N, 16.87.

EXAMPLE 22

2,9-dimethyl-3-(1-pyrrolidinylmethyl)-9H-dibenzo[b,f]imidazo[1,2-d][1,4]diazepine hydrobromide In a 50-ml. round bottom flask, 1.32 g. of 2-methyl-3-[1-pyrrolidinylmethyl]-9H-dibenzo[b,f]imidazo [1,2-a][1,4]diazepine (4.00 mmol.) is dissolved in 5.24 g. of an 88% formic acid (60.0 mmol.) solution. To it is added 5.4 ml. (36.0 mmol.) of a 37% aqueous formalin solution. The mixture is heated on a steam bath for 24 hours under a nitrogen atmosphere. The entire reaction mixture is quenched in a 5% aqueous sodium hydroxide solution and extracted with chloroform. The chloroform layer is washed twice with water and dried over anhydrous sodium sulfate. The solvent is removed in vacuo to yield 800 mg. of a yellow oily residue. The product is separated from minor amounts of impurities by column chromatography (silica gel, using 3% methanol-97% chloroform as eluent) to yield 300 mg. of oil. The oil is converted to its hydrobromide salt and crystallized from methanol-ethyl acetate to afford 150 mg. of 2,9-dimethyl-3-(1-pyrrolidinylmethyl)-9H-dibenzo-[b,f]imidaze[1,2-d][1,4]diazepine hydrobromide of melting point 198°–200° C.

Anal. calcd. for $C_{22}H_{25}BrN_4$: C, 62.12; H, 5.93; N, 13.17. Found: C, 62.09; H, 5.96; N, 13.00.

EXAMPLE 23

2-Methyl-3-(1-morpholinylmethyl)-9H-dibenzo-[b,f]imidazo[1,2-d][1,4]diazepine

In a 100-ml. round bottom flask, 2.5 g. (10.0 mmol.) of 2-methyl-9H-dibenzo[b,f]imidazo[1,2-d][1,4]diazepine is dissolved in 20 ml. of monoglyme and treated with 6.0 ml. (2.25 g., 74.0 mmol.) of a 37% aqueous formalin solution, 2.60 g. (30.0 mmol.) of morpholine and 15 ml. of a 2N hydrochloric acid solution. The solution is stirred for 18 hours on a steam bath under a nitrogen atmosphere. The reaction is quenched in a cold aqueous 10% sodium hydroxide solution and the product is extracted with chloroform. The chloroform layer is washed twice with water and dried over anhydrous sodium sulfate. After drying, it is filtered and concentrated in vacuo to give 3.0 g. of a tan oil, which is chromatographed over 300 g. of silica gel using a 3% methanol-97% chloroform solution as eluent to afford 2.5 g. of a yellow oil. On trituration with ether, 1.0 g. of a tan powder is obtained of melting point 180°–185° C. The ether solution, on cooling, affords 700 mg. of 2-methyl-3-(1-morpholinylmethyl)-9H-dibenzo[b,f]-imidazo[1,2-d][1,4]diazepine of melting point 182°–184° C. This latter fraction is crystallized from ethanol to afford 550 mg. of prisms of melting point 218°–219° C.

Anal. calcd. for $C_{21}H_{22}N_4O$: C, 70.38; H, 7.19; N, 14.28. Found: C, 70.08; H, 7.12; N, 14.12.

EXAMPLE 24

3.9-Dimethyl-2-hydroxymethyl-9H-dibenzo[b,f]-imidazo[1,2-d][1,4]diazepine

In the manner given in example 19 3-methyl-9H-dibenzo[b,f]imidazo[1,2-d][1,4]diazepine is dissolved in 88% formic acid, treated with 37% aqueous formalin solution and heated for 24 hours, to give 3,9-dimethyl-2-hydroxymethyl-9H-dibenzo [b,f]-imidazo[1,2-d][1,4]diazepine.

EXAMPLE 25

3,9-Dimethyl-2-(4-methyl-1-piperazinyl) methyl-9H-dibenzo[b,f]-imidazo[1,2-d][1,4]-diazepine A sampmle of 3,9-dimethyl-2-hydroxymethyl-9H-dibenzo[b,f]-imidazo[1,2-d][1,4]diazepine is suspended in a chloroform/tetrahydrofuran mixture and treated with triethylamine. After cooling to −20° C. methanesulfonyl chloride is added with stirring at −20° C. The mixture is treated with 4-methylpiperazine and warmed gradually to room temperature. Work-up from an aqueous base followed by the usal purification techniques affords the product 3,9-dimethyl-2-(4-methyl-1-piperazinyl)methyl-9H-dibenz[b,f]-imidazo[1,2-d][1,4]diazepine as a yellow oil.

Treatment of the compounds of the formula III (which includes IIIA, IIIB, IIIC, IIID, IIIE, IIIF, IIIG, IIIH, III(I), and IIIJ) with pharmacologically acceptable acids preferably in a solvent e.g. water, ethanol, ether, dioxane and the like, provides the pharmacologically acceptable acid addition salts of these 9H-dibenzoimidazodiazepine compounds. Examples of such addition salts are the hydrochlorides, fumarates, hydrobromides, hydriodides, sulfates, methanesulfonates, toluenesulfonates, citrates, tartrates, lactates, palmoates, laurates, acetates, succinates, and the like.

I claim:

1. A compound of the formula

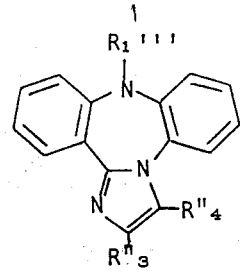

wherein $R_1'''$ is hydrogen or alkyl of 1 to 3 carbon atoms, inclusive; and wherein one of the parameters $R''_3$ or $R''_4$ is

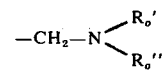

and the other one is hydrogen or alkyl as defined above; wherein $R_o'$ and $R_o''$ are hydrogen or alkyl defined as above, or together

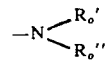

is pyrrolidino, piperidino, N-methylpiperazino, or morpholino and the pharmacologically acceptable acid addition salts thereof.

2. The compound according to claim 1, wherein $R''_3$ is methyl, $R''_4$ is 1-pyrrolidinyl methyl, $R_1'''$ is hydrogen and the compound is therefore 2-methyl-3-(1-pyrrolidinyl-methyl)-9H-dibenzo[b,f]imidazo[1,2-d][1,4]diazepine.

3. The compound according to claim 1, as a hydrobromide wherein $R_1'''$ and $R''_3$ are methyl, $R''_4$ is 1-pyrrolidinylmethyl and the compound is therefore 2,9-dimethyl-3-(1-pyrrolidinylmethyl)-9H-dibenzo[b,f]imidazo[1,2-d][1,4]diazepine hydrobromide.

4. A compound according to claim 1, wherein $R_1'''$ is hydrogen, $R''_3$ is 2-methyl, $R''_4$ is 1-morpholinyl methyl and the compound is therefore 2-methyl-3-(1-morpholinylmethyl)-9H-dibenzo[b,f]imidazo[1,2-d][1,4]diazepine.

5. A compound according to claim 1, wherein $R_1'''$ and $R_4$ are methyl, $R_2$ is (4-methyl-1-piperazinyl)-methyl and the compound is therefore 3,9-dimethyl-2-[(4-methyl-1-piperazinyl)methyl]-9H-dibenzo[b,f]imidazo[1,2-d][1,4]diazepine.

* * * * *